US00PP28503P3

(12) United States Plant Patent
Yoshiie

(10) Patent No.: US PP28,503 P3
(45) Date of Patent: Oct. 10, 2017

(54) APPLE TREE NAMED 'SHINKU'

(50) Latin Name: *Malus domestica*
Varietal Denomination: Shinku

(71) Applicant: Kazuo Yoshiie, Nagano (JP)

(72) Inventor: Kazuo Yoshiie, Nagano (JP)

( * ) Notice: Subject to any disclaimer, the term of this patent is extended or adjusted under 35 U.S.C. 154(b) by 0 days.

(21) Appl. No.: 14/998,617

(22) Filed: Jan. 21, 2016

(65) Prior Publication Data

US 2016/0219768 P1 Jul. 28, 2016

Related U.S. Application Data

(60) Provisional application No. 62/107,220, filed on Jan. 23, 2015.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — Lathrop & Gage LLP

(57) ABSTRACT

A new and distinct apple variety is described, the variety results from controlled cross pollination between (Jonathan× Pink Pearl)×Fuji. The fruit of the apple tree of this new variety has an attractive appearance characterised by its large size (over 300 gms in Japan) red flesh and radiant red pink color (100%) with dark red sporadic stripes. The new variety has been named 'Shinku'.

3 Drawing Sheets

CROSS REFERENCE TO RELATED APPLICATION

This application claims the benefit of U.S. Provisional Application No. 62/107,220 filed Jan. 23, 2015, the disclosure of which is incorporated by reference in its entirety.

Genus and species plant claimed: *Malus domestica.*

Variety denomination: 'Shinku'.

BACKGROUND OF THE INVENTION

The present invention relates to a new and distinct variety of *Malus domestica* hereinafter referred to by the cultivar name 'Shinku'. The new plant variety described herein resulted from controlled cross pollination between (Jonathan×Pink Pearl)×Fuji performed in 2005 in Nagano prefecture, Japan. The controlled cross was performed in the inventor's apple orchard. Approximately 300 hybrid seeds were sown in the spring of 2006, and top grafting on 16 year-old Fuji trees ('CG24' rootstock) was performed using their scions in spring of 2007 in Nagano. The year of first bearing was 2011 and the variety was selected in 2012. The new variety was determined to be distinct from the parent varieties.

SUMMARY OF THE INVENTION

This variety can be characterized by its large size (over 300 gms grown in Japan) red flesh and radiant red pink color (100%) with dark red sporadic stripes. 'Shinku' displays bright white lenticels and often has an open calyx. The new variety has been named 'Shinku'. 'Shinku' was asexually reproduced and is currently grown in Japan under Japanese conditions.

Shinku was determined to be distinct from the parent varieties 'Irodori' (Jonathan×Pink Pearl) and 'Fuji', as well as the closely related varieties. 'Moon Rouge' and 'Enbu' by the following characteristics. 'Shinku' has conic fruit shape compared with 'Irodori' which has obloid fruit shape. Harvest period of 'Shinku' is early/mid October compared with Irodori which is late October. 'Shinku' has red colored fruit fresh compared with 'Fuji' which does not. 'Shinku' has earlier harvest (early/mid October) than 'Enbu' (early November). 'Shinku' has red colored fruit skin compared with 'Moon Rouge' which has yellow colored fruit skin. 'Shinku' have red colored fruit skin compared with 'Pink Pearl' which has yellow colored fruit skin.

BRIEF DESCRIPTION OF THE DRAWINGS

The accompanying photographs show typical specimens of the tree, foliage and fruit of the new variety as depicted in colours as nearly true as is reasonably possible to make the same in a colour illustration of this character.

DETAILED DESCRIPTION

Figure 1:
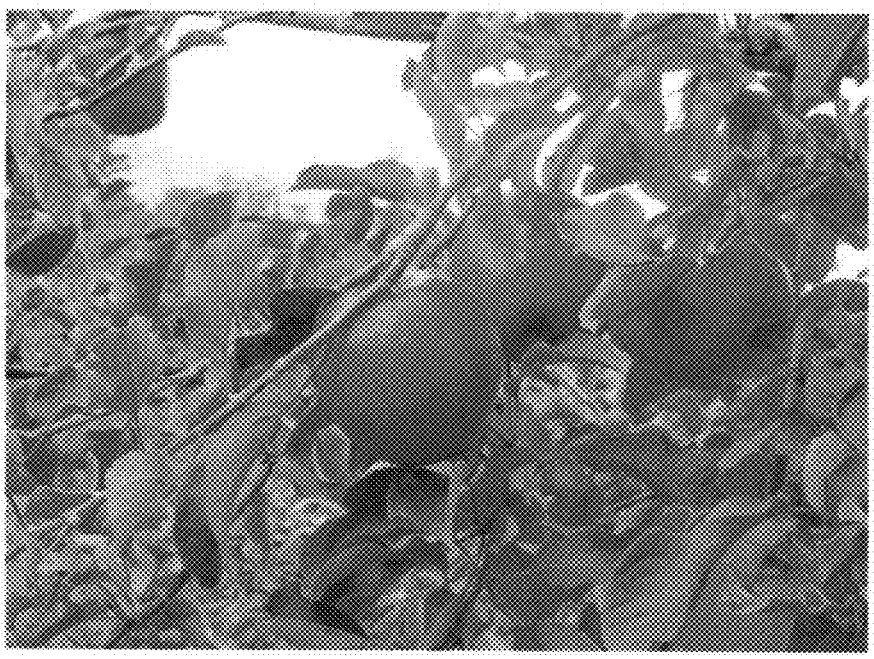
FIG. 1 shows fruit and foliage on the tree
Figure 2:
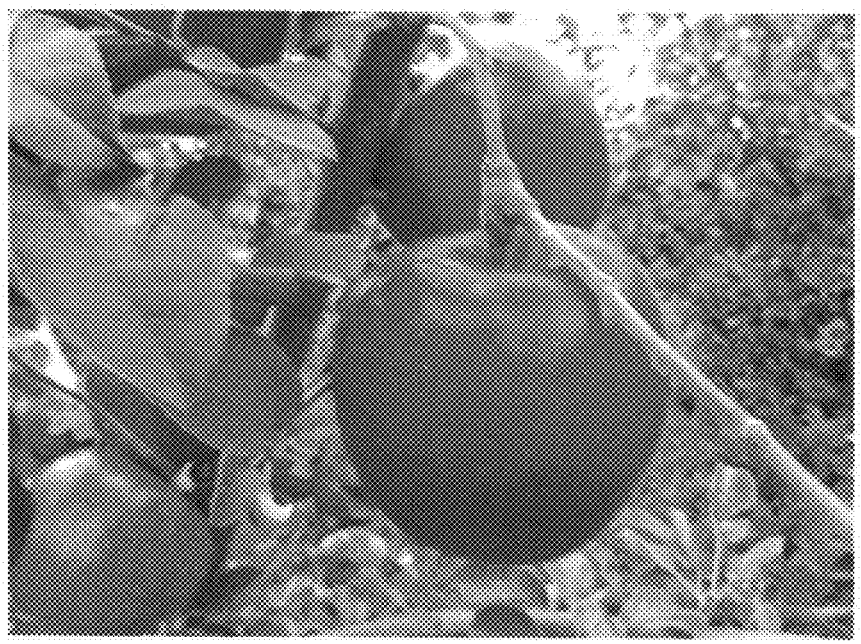
FIG. 2 shows a close up view of fruit and foliage on the tree
Figure 3:
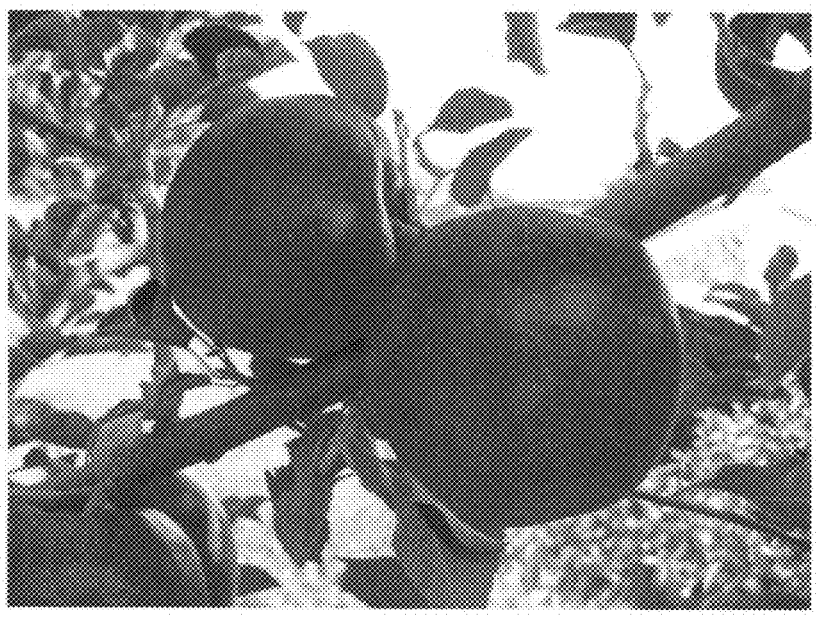
FIG. 3 shows a close up view of fruit on the tree
Figure 4:
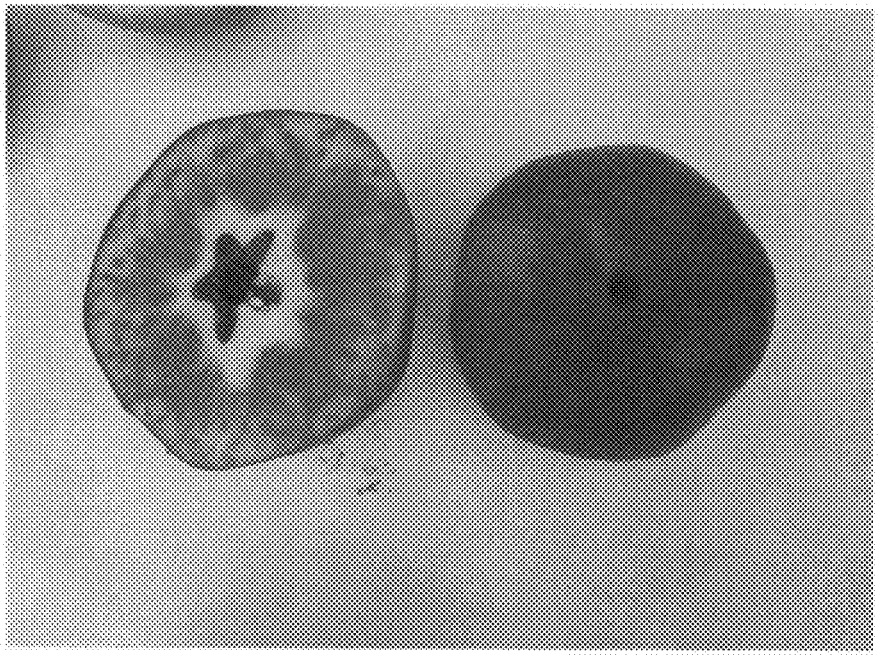
FIG. 4 shows uncut and fruit and transverse sections through fruit
Figure 5:
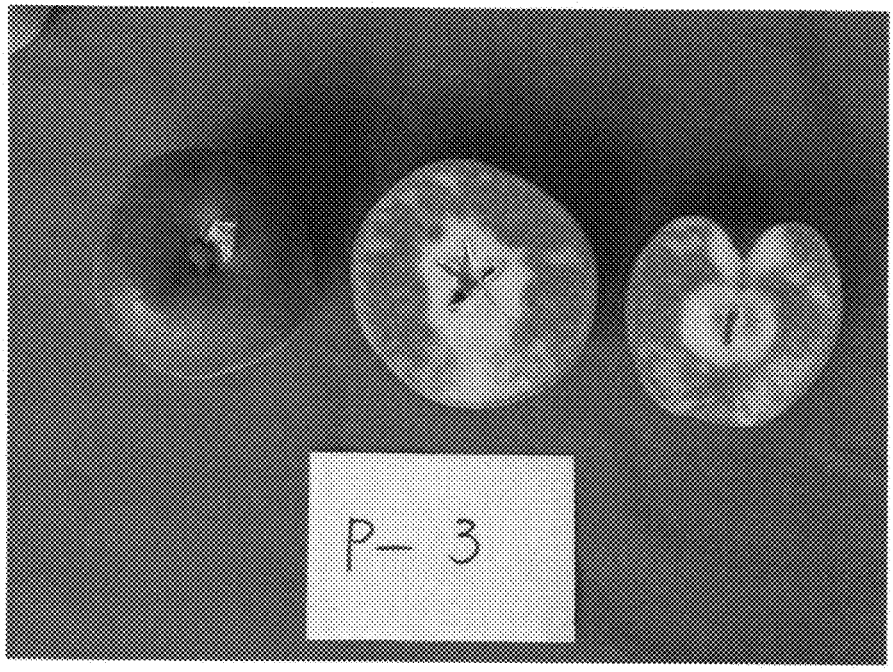
FIG. 5 shows uncut and fruit, and transverse and longitudinal sections through fruit

The following botanical description is based on observations made during the 2013 growing season in Nagano prefecture, Japan. The observations are based on top grafted (8 year-old) branches on 16 year-old 'Fuji'/CG24. Color observations are made in accordance with the Japan Horticultural Standard Color Chart (JHSCC). The following is a detailed description of the new variety:

Plant description:

*Breeding*.—Produced by controlled pollination. Parents: (Jonathan×Pink Pearl)×Fuji. Pollination self-incompatibility group: S3S5. Method of propagating the variety: vegetative propagation through grafting.

*Tree type*.—Ramified. Tree habit: spreading. Trunk (bark): grayish brown, 1016 (JHSCC). Branches: grayish brown, 1016 (JHSCC). Height (5 year old tree): 3.6 m. Trunk diameter (at 30 cm above the graft) 7.6 cm.

Foliage description:

*Length of internode* (*one-year-old shoot*).—Short (2.3 cm). Number of lenticels (one-year-old shoot): medium. Lenticel shape: round. Lenticel number/$cm^2$: 12.1. Lenticel color: light gray, 02 (JHSCC). Color (one year-old shoot): dark grayish brown, 1318 (JHSCC).

*Leaf blade attitude in relation to shoot*.—Upwards. Leaf blade length: medium (7.7 cm). Leaf blade width: medium (5.3 cm). Leaf blade ratio length/width: medium (1.45). Leaf color: deep yellow green, 4006 (JHSCC).

*Petiole length*.—Short (2.1 cm).

Flower description:

*Predominant color at balloon stage*.—Bright red, 0106 (JHSCC). Diameter with petals pressed into horizontal position: very small (3.0 cm). Arrangement of petals: free. Time of beginning of flowering (10% open flowers): early.

Fruit:

*Fruit size*.—Large. Weight (286 g under Japanese cultivating technique). Height: medium (7.7 cm). Diameter: large (9.0 cm). Ratio height/diameter: large (0.86). Size of eye: small. Bloom of skin: absent or weak. Intensity of over color: weak with sporadic stripe. Area of russet around stalk attachment: absent or small. Area of russet around eye basin: absent or small. Fruit skin color: deep red, 0408 (JHSCC).

*Length of stalk*.—Short (1.4 cm) Thickness of stalk: medium (3.3 mm). Depth of stalk cavity: deep (1.9 cm). Width of stalk cavity: broad (4.7 cm). Depth of eye basin: shallow (0.4 cm). Width of eye basin: medium (3.6 cm).

*General shape of fruit*.—Conic. Relative area of over colour of fruit: absent or very small (Granny Smith). Observed dates for harvest period: early/mid October, Nagano prefecture, Japan. Hue of under colour: purple red (Spartan). Pattern of over colour: only stripes, no flush (Royal Gala). Width of stripes: medium (Royal Gala). Time of eating maturity: late (Fuji). Color of flesh: vivid purplish red, 9707 (JHSCC). Acidity of flesh is low. Titlate acidity: 0.47%. Soluble solids: 14.7%. Firmness: 15.5 lb.

*Duration of storage*.—Common and cold storage is very long. Cold storage: one month. Shelf life: one week.

*Disease susceptibility*.—No known resistances to pests and diseases.

I claim:

1. A new and distinct apple tree substantially as illustrated and described herein.

* * * * *